(12) United States Patent
Schmidt (10) Patent No.: US 9,113,800 B2
(45) Date of Patent: Aug. 25, 2015

(54) METHOD FOR VISUALIZING A LYMPH NODE AND CORRESPONDINGLY EMBODIED COMBINED MR/PET APPARATUS

(75) Inventor: Sebastian Schmidt, Weisendorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 324 days.

(21) Appl. No.: 13/187,743

(22) Filed: Jul. 21, 2011

(65) Prior Publication Data

US 2012/0035461 A1 Feb. 9, 2012

(30) Foreign Application Priority Data

Aug. 6, 2010 (DE) .......................... 10 2010 033 610

(51) Int. Cl.
*A61B 6/03* (2006.01)
*A61B 5/00* (2006.01)
(Continued)

(52) U.S. Cl.
CPC ................ *A61B 6/037* (2013.01); *A61B 5/415* (2013.01); *A61B 5/418* (2013.01); *A61B 6/4417* (2013.01);
(Continued)

(58) Field of Classification Search
CPC ........ A61B 5/415; A61B 5/418; A61B 6/037; A61B 6/4417; A61B 6/5247; G01R 33/481; G06T 2207/10088; G06T 2207/10104; G06T 2207/20221; G06T 2207/30004; G06T 5/50; G06T 7/0014
USPC ........... 600/407, 410, 411, 425, 431; 382/128
See application file for complete search history.

(56) References Cited

U.S. PATENT DOCUMENTS 8,073,525 B2 12/2011 Ladebeck et al.
8,285,357 B2 * 10/2012 Gardner et al. ............... 600/407
(Continued)

FOREIGN PATENT DOCUMENTS

CN 1839757 A 10/2006
CN 1919147 A 2/2007
(Continued)

OTHER PUBLICATIONS

Domingues et al., "Whole-Body MRI and FDG PET Fused Images for Evaluation of Patients with Cancer", AJR, Apr. 2009, pp. 1012-1020.*
(Continued)

*Primary Examiner* — Katherine Fernandez
(74) *Attorney, Agent, or Firm* — Harness, Dickey & Pierce, P.L.C.

(57) ABSTRACT

A method is disclosed for visualizing a lymph node in a volume section of an examination subject by way of a combined MR/PET apparatus and to a correspondingly embodied combined MR/PET apparatus. The method includes acquisition of PET data of the volume section by way of a positron emission detector in order to record on the basis of the PET data a metabolic activity per PET voxel within the predetermined volume section; acquisition of MR data of the volume section by way of a magnetic resonance system in order to record on the basis of the MR data a lymph-node-specific contrast per region of the predetermined volume section; and generation of an image as a function of the metabolic activity recorded per PET voxel and as a function of the lymph-node-specific contrast recorded per region, abnormal lymph nodes being visualized in the image as distinguishable from normal lymph nodes.

16 Claims, 2 Drawing Sheets

(51) Int. Cl.
    *A61B 6/00* (2006.01)
    *G01R 33/48* (2006.01)
    *G06T 5/50* (2006.01)
    *G06T 7/00* (2006.01)

(52) U.S. Cl.
    CPC ............ *A61B 6/5247* (2013.01); *G01R 33/481* (2013.01); *G06T 5/50* (2013.01); *G06T 7/0014* (2013.01); *G06T 2207/10088* (2013.01); *G06T 2207/10104* (2013.01); *G06T 2207/20221* (2013.01); *G06T 2207/30004* (2013.01)

(56) References Cited

U.S. PATENT DOCUMENTS

| | | | | |
|---|---|---|---|---|
| 2006/0251312 | A1* | 11/2006 | Krieg et al. | 382/131 |
| 2007/0189445 | A1 | 8/2007 | Haras et al. | |
| 2008/0021301 | A1* | 1/2008 | Gonzalez et al. | 600/407 |
| 2010/0134106 | A1* | 6/2010 | Huwer | 324/309 |
| 2010/0232667 | A1* | 9/2010 | Azar et al. | 382/131 |

FOREIGN PATENT DOCUMENTS

| | | |
|---|---|---|
| CN | 101023876 A | 8/2007 |
| CN | 101732049 A | 6/2010 |

OTHER PUBLICATIONS

Misselwitz, "MR contrast agents in lymph node imaging", European Journal of Radiology, 2006, pp. 375-382.*
Proulx et al., "Longitudinal Assessment of Synovial,Lymph Node, and Bone Volumes in Inflammatory Arthritis in Mice by In Vivo Magnetic Resonance Imaging and Microfocal Computed Tomography", Arthritis & Rheumatism, vol. 56, No. 12, Dec. 2007, pp. 4024-4037.*
Keereman et al., "MRI-Based Attenuation Correction for PET/MRI Using Ultrashort Echo Time Sequences", The Journal of Nuclear Medicine, vol. 51, No. 5, May 2010, pp. 812-818.*
Shetty et al., "Magnetic resonance techniques in lymph node imaging", Jul. 9, 2004. URL: http://www.appliedradiology.com/articles/magnetic-resonance-techniques-in-lymph-node-imaging.*
Tatsumi et al., "Preoperative diagnosis of lymph node metastases in gastric cancer by magnetic resonance imaging with ferumoxtran-10", Gastric Cancer, 2006, pp. 120-128.*
Kitagawa et al., "Prospective Comparison of 18-F-FDG PET with Conventional Imaging Modalities (MRI, CT, 67-Ga Scintigraphy) in Assessment of Combined Intraarterial Chemotherapy and Radiotherapy for Head and Neck Carcinoma", The Journal of Nuclear Medicine, vol. 44, No. 2, Feb. 2003, pp. 198-206.*
Seok-Ki Kim, et.al.: "Additional value of MR/PET fusion compared with PET/CT in the detection of lymph node metastases in cervical cancer patients", in: European Journal of Cancer, vol. 45, Issue 12, Aug. 2009, pp. 2103-2109; Others; 2009.
P. Wunderbaldinger, et.al.: "Experimentelle and klinische Ansätze zur Lymphknotenbildgebung", in: Der Radiologe, Feb. 1, 2001, Publisher: Springer Berlin/Heidelberg, vol. 41, Issue 2, pp. 121-130, ISSN 0033-832X: Others; 2001.
Domingues, Roberto C. et al: "Whole-Body MRI and FDG PET Fused Images for Evaluation of Patients with Cancer", AJR, Apr. 2009, pp. 1012-1020.
Misselwitz, Bernd; "MR contrast agents in lymph node imaging", European Journal of Radiology, 2006, pp. 375-382; 2006; Jun. 30, 2006.
Proulx, Steven et al; "Longitudinal Assessment of Synovial,Lymph Node, and Bone Volumes in Inflammatory Arthritis in Mice by In Vivo Magnetic Resonance Imaging and Microfocal Computed Tomography", Arthritis & Rheumatism, vol. 56, No. 12, pp. 4024-4037; 2007; Dec. 31, 2007.
Keereman, Vincent et al: "MRI-Based Attenuation Correction for PET/MRI Using Ultrashort Echo Time Sequences", The Journal of Nuclear Medicine, vol. 51, No. 5, May 2010, pp. 812-818.
Ying-Ying, Hu et al: "F-FDG PET/CT for the detection of primary tumors metastasizing to lymph nodes of the neck"; in "Cancer", vol. 28, No. 3, pp. 312-317; 2009; Dec. 31, 2009.
Yoshiharu, Ohno et al:.; "STIR Turbo SE MR Imaging vs. Coregistered FDG-PET/CT: Quantitative and Qualitative Assessment of N-Stage in Non-Small-Cell Lung Cancer Patients"; in Journal of magnetic resonance imaging; vol. 26, No. 4, pp. 1071-1080; 2007; Oct. 31, 2007.
Sironi, Sandro: "Lymph Node Metastasis in Patients with Clinical Early-Stage Cervical Cancer: Detection with Integrated FDG PET/CT"; in Radiology, vol. 238, No. 1, pp. 272-279; 2006; Jan. 31, 2006.
Zhao, Xiaochun et al: "Initial exploration of pelvic lymph node detection with MR whole-body diffusion imaging", in: Sectional anatomy, vol. 28, No. 1; 2010; Apr. 14, 2010.

* cited by examiner

FIG 1

METHOD FOR VISUALIZING A LYMPH NODE AND CORRESPONDINGLY EMBODIED COMBINED MR/PET APPARATUS

PRIORITY STATEMENT

The present application hereby claims priority under 35 U.S.C. §119 on German patent application number DE 10 2010 033 610.6 filed Aug. 6, 2010, the entire contents of which are hereby incorporated herein by reference.

FIELD

At least one embodiment of the present invention relates to a method for visualizing a lymph node, in particular a malignant lymph node, in a predetermined volume section of a patient by way of a combined MR/PET apparatus, as well as to a correspondingly embodied combined MR/PET apparatus.

BACKGROUND

As background information, assessing lymph nodes in malignant diseases (cancers) in diagnostic radiology is a major problem and one that continues to remain unresolved. The contemporary approach is based on the principle that lymph nodes with a size of more than 10 mm harbor malignancy and that lymph nodes that are less than 10 mm are benign (inoffensive). This crude morphological classification is not always correct, however, since of course lymph nodes less than 10 mm in size can also be affected by tumor cells and since lymph nodes more than 10 mm in size can also be simply enlarged due to an inflammatory change and therefore do not harbor malignancy. Furthermore there also exist fibrotic lymph nodes which have been converted into connective tissue as a result of a previous inflammation process and consequently are likewise enlarged.

Positron emission tomography (PET) is frequently used in the prior art for diagnosing lymph nodes. After a tracer, fluorodeoxyglucose (FDG) for example, has been administered, PET visualizes the local activity of the glucose metabolism, which is significantly increased in the case of malignant diseases. A disadvantageous aspect, however, is that the activity of the glucose metabolism is also increased in the case of inflammations, which means that a malignant disease cannot be inferred on the basis of an increase in the activity of the glucose metabolism. Although the use of the tracer fluorothymidine (FLT) in PET reveals a higher specificity for malignant diseases, it likewise proves unsuccessful very frequently in the case of lymph nodes. Trials with other PET tracers, based on 11C-choline for example, have similarly failed to produce good results to date and consequently they are not employed commercially.

Moreover, using PET for diagnosing lymph nodes is problematic due to the low spatial resolution. In PET, a small lymph node is usually not clearly visible due to the partial volume effect. As a result of the partial volume effect objects are represented with too little activity concentration in the PET image if their size is in the range of the PET resolution or below.

Equally, the combined use of PET and computed tomography (CT) achieves no further advantage compared to PET on its own in relation to this problem, since CT merely allows a judgment concerning the size of the lymph node and furnishes no information on the reason for the enlargement (e.g. malignant event).

As background information, magnetic resonance tomography (MRT) is likewise only able to deliver judgments relating to the size of a lymph node, since experiments, by way of MR spectroscopy for example, to deliver judgments concerning the malignancy of a lymph node have so far yielded no satisfactory results. Also known are lymphotropic contrast agents for MRT which are taken up by inflammatory cells and selectively accumulate in the lymphatic tissue. Examples of contrast agents of the type are iron oxides, such as Sinerem (Guerbet) and perfluorocarbons (experimental contrast agents). However, the contrast agents likewise do not lead in every case to a correct diagnosis, since they merely indicate if inflammatory cells (macrophages) are present in a lymph node and give no direct pointer to whether malignant cells are contained in a lymph node. If a lymph node is fibrotic and contains neither macrophages nor tumor cells, the use of such contrast agents can lead to an incorrect diagnosis in that the lymph node is wrongly classified as cancerous.

The use of iron oxides as contrast agents results in a further disadvantage, since iron oxide leads to a negative contrast (to a local signal loss) so that the lymph nodes are no longer visible. For the assessment according to the prior art it is therefore necessary to acquire a second MR image which is generated before the contrast agent is administered (i.e. at least 24 hours previously). Since the lymph nodes can shift position within the course of 24 hours (i.e. between the generation of the two MR images), a corresponding evaluation is problematic. Other MR contrast agents (e.g. gadolinium chelates) produce only a very unspecific contrasting of the lymph nodes and therefore lead to no satisfactory results in the assessment of the malignancy.

SUMMARY

At least one embodiment of the present invention is directed to visualizing lymph nodes in such a way that an abnormal lymph node (in particular a lymph node harboring a malignant disease) can be identified from the visualization (from the image).

At least one embodiment of the invention is directed to a method for visualizing a lymph node, a combined MR/PET apparatus, a computer program product, and/or by an electronically readable data medium. The dependent claims define preferred and advantageous embodiment variants of the present invention.

Within the scope of at least one embodiment of the present invention, a method is provided for visualizing a lymph node in a predetermined volume section of an examination subject, i.e. a patient, by way of a combined MR/PET apparatus. At least one embodiment of the inventive method includes the following:

In a first step, PET data of the predetermined volume section is acquired by way of a positron emission detector, a metabolic activity (e.g. an activity of the glucose metabolism) per PET voxel within the predetermined volume being recorded with the aid of the PET data. In order to record the metabolic activity, in particular a tracer (e.g. fluorodeoxyglucose) is administered prior to the acquisition of the PET data.

In a second step, MR data of the predetermined volume section is acquired by way of a magnetic resonance system, a contrast specific to lymph nodes (i.e. the lymph nodes differ in terms of contrast from the remainder of the predetermined volume section) per region of the predetermined volume being recorded with the aid of the MR data. The lymph-node-specific contrast is achieved in particular through the administration of a lymphotropic contrast agent (iron oxide or perfluorocarbon for example) prior to the acquisition of the MR data.

According to at least one embodiment of the invention, the first step can be performed before the second step, the second step before the first step or the first step simultaneously with the second step.

In a third step, an image is generated as a function of the metabolic activity recorded per PET voxel and as a function of the lymph-node-specific contrast recorded per region. In the process abnormal lymph nodes are visualized in said image so as to be distinguishable from normal lymph nodes.

Also provided within the scope of an embodiment of the present invention is a combined MR/PET apparatus for generating an image of a lymph node in a predetermined volume section in an examination subject. In this case the MR/PET apparatus comprises a control unit for controlling a positron emission detector and for controlling a magnetic resonance system and an image computing unit for receiving PET data of the predetermined volume section acquired by the positron emission detector, for receiving MR data of the predetermined volume section recorded by the magnetic resonance system and for generating the image from the PET data and the MR data.

An embodiment of the present invention also describes a computer program product, in particular a computer program or a piece of software which can be loaded into a memory of a programmable controller or of a computing unit of a combined MR/PET apparatus. All or different above-described embodiments variants of the method according to the invention can be performed by way of the computer program product when the computer program product runs in the controller or control device of the combined MR/PET apparatus. In this case the computer program product possibly requires program segments, e.g. libraries and help functions, in order to implement the corresponding embodiment variants of the methods. In other words, it is intended by way of the claim directed to the computer program product to place under protection in particular a computer program or a piece of software by which one of the above-described embodiment variants of the method according to the invention can be performed or, as the case may be, which implements said embodiment variant. The software in this case can be a source code (e.g. C++) which still has to be compiled (translated) and link-edited or which only needs to be interpreted, or it can be an executable software code which for execution purposes simply needs to be loaded into the corresponding computing unit.

Finally, at least one embodiment of the present invention discloses an electronically readable data medium, e.g. a DVD, a magnetic tape or a USB stick on which electronically readable control information, in particular software (cf. above), is stored. When the control information (software) is read from the data medium and stored in a controller or computing unit of a combined MR/PET apparatus, all the inventive embodiment variants of the above-described method can be performed.

BRIEF DESCRIPTION OF THE DRAWINGS

The present invention is described in detail below with the aid of example embodiment variants and with reference to the figures, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments.

The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/ or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
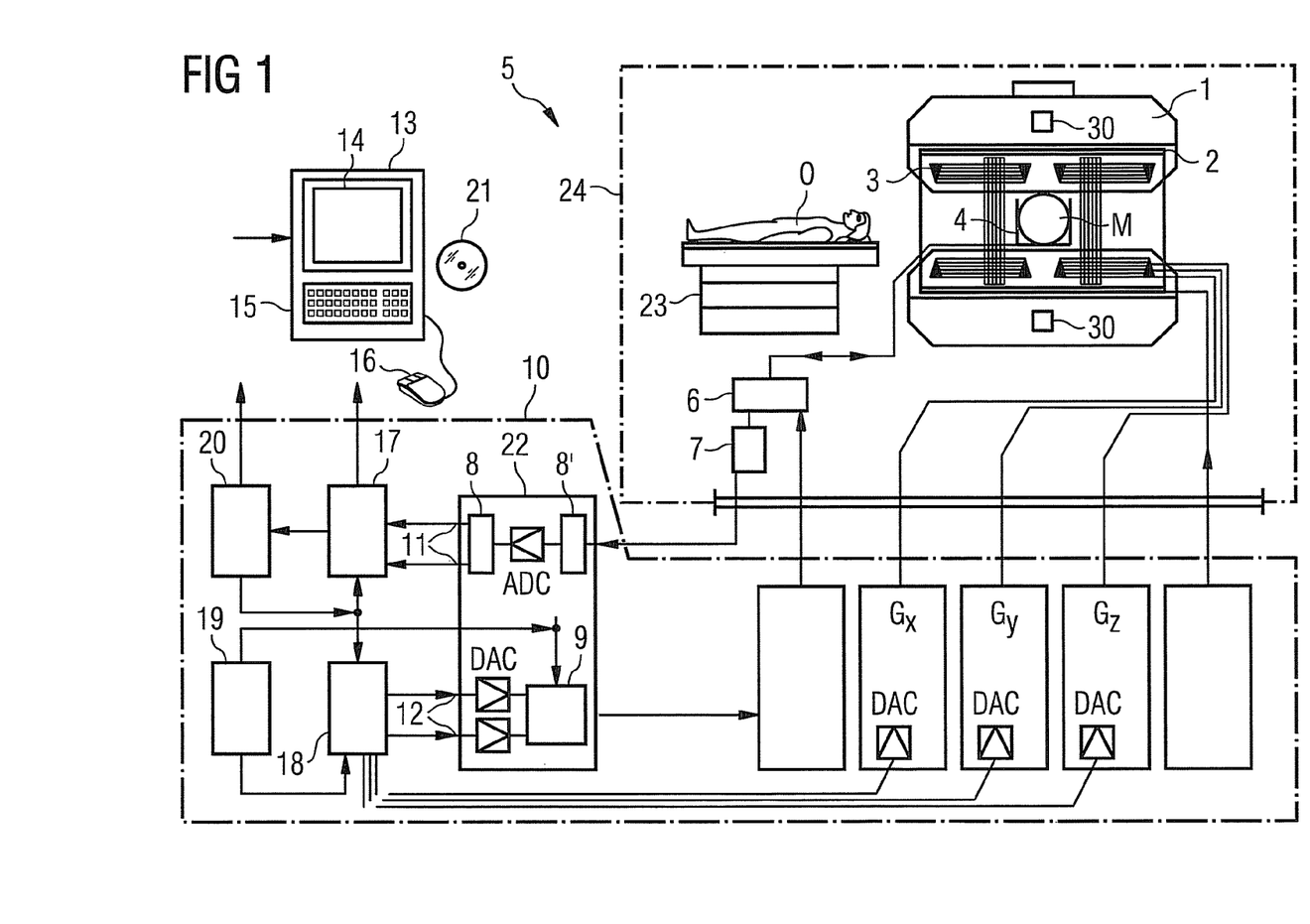
FIG. 1 is a schematic representation of a combined MR/PET apparatus according to an embodiment of the invention.

FIG. 1 shows a schematic representation of a combined MR/PET apparatus 5 which comprises a positron emission detector 30 and a magnetic resonance system 24. In this arrangement a basic field magnet 1 of the magnetic resonance system 24 generates a strong, temporally constant magnetic field for polarizing or aligning the nuclear spins in an examination region of a subject O, such as e.g. a part of a human body that is to be examined, which, lying on a table 23, is introduced into the magnetic resonance system 24 for the purpose of generating an image. The high degree of homogeneity of the basic magnetic field that is required for the nuclear magnetic resonance measurement is defined in a typically spherical measurement volume M in which the parts of the human body that are to be examined are arranged for the purpose of the MR data acquisition. So-called shim plates made of ferromagnetic material are fitted at suitable points in order to support the homogeneity requirements and in particular in order to eliminate time-invariable effects. Time-variable effects are eliminated by way of shim coils 2.

A cylindrical gradient coil system 3 including three part-windings is installed in the basic field magnet 1. Each part-winding is supplied with current by an amplifier for the purpose of generating a linear (also time-variable) gradient field in the respective direction of the Cartesian coordinate system. In this case the first part-winding of the gradient field system 3 generates a gradient $G_x$ in the x-direction, the second part-winding a gradient $G_y$ in the y-direction and the third part-winding a gradient $G_z$ in the z-direction. The amplifier includes a digital-analog converter which is controlled by a sequence controller 18 for generating gradient pulses at the correct time.

Contained within the gradient field system 3 are one or more radio frequency antennas 4 which convert the radio frequency pulses emitted by a radio frequency power amplifier into a magnetic alternating field for exciting the nuclei and aligning the nuclear spins of the subject O to be examined or of the region of the subject O to be examined. Each radio frequency antenna 4 includes one or more RF transmit coils and one or more RF receive coils in the form of an annular, preferably linear or matrix-shaped array of component coils. The alternating field originating from the preceding nuclear spins, i.e. usually the nuclear spin echo signals induced by a pulse sequence including one or more radio frequency pulses and one or more gradient pulses, is also converted by the RF receive coils of the respective radio frequency antenna 4 into a voltage (measurement signal) which is supplied via an amplifier 7 to a radio frequency receive channel 8 of a radio frequency system 22. The radio frequency system 22 additionally comprises a transmit channel 9 in which the radio frequency pulses for exciting the magnetic nuclear resonance are generated. In this case the respective radio frequency pulses are represented digitally as a sequence of complex numbers as a result of a pulse sequence specified by the system computer 20 in the sequence controller 18. This number sequence is supplied as a real and an imaginary part via one input 12 in each case to a digital-analog converter in the radio frequency system 22 and by the latter to a transmit channel 9. In the transmit channel 9 the pulse sequences are modulated onto a radio frequency carrier signal whose fundamental frequency corresponds to the resonant frequency of the nuclear spins in the measurement volume.

The switchover from transmit to receive operation is effected via a duplexer 6. The RF transmit coils of the radio frequency antenna(s) 4 radiate the radio frequency pulses for exciting the nuclear spins into the measurement volume M and resulting echo signals are sampled via the RF receive coil(s). The correspondingly obtained nuclear magnetic resonance signals are demodulated in the receive channel 8' (first demodulator) of the radio frequency system 22 phase-sensitively onto an intermediate frequency and digitized in the analog-digital converter (ADC). The signal is additionally demodulated onto the frequency 0. The demodulation onto the frequency 0 and the separation into real and imaginary part take place following the digitization in the digital domain in a second demodulator 8. An MR image and a PET image (see below) are reconstructed by an image computer 17 from the measurement data thus obtained. The management of the measurement data, the image data and the control programs is handled via the system computer 20. Based on a specification by way of control programs, the sequence controller 18 controls and monitors the generation of the pulse sequences desired in each case and the corresponding sampling of the k-space. In particular the sequence controller 18 controls the switching of the gradients at the correct time, the transmission of the radio frequency pulses at a defined phase amplitude and the reception of the nuclear magnetic resonance signals. The time base for the radio frequency system 22 and the sequence controller 18 is provided by a synthesizer 19.

As already stated in the foregoing, the MR/PET apparatus 5 comprises a positron emission detector 30 which in most cases is embodied as annular. The tracers used in PET are marked by way of a positron emitter. As the positron emitter decays in the tissue of the patient O, two y quanta are generated close to the site of the corresponding positron emission as a result of an annihilation and fly apart in opposite directions. If the two y quanta are measured by two oppositely disposed detector elements of the positron emission detector 30 within a predetermined coincidence time interval, the annihilation site can be pinpointed to a position on the connecting line between the two detector elements.

The positron emission detector 30 is used to acquire the PET data from which the PET image is then generated in the image computer 17. The PET image is inventively combined with the MR image in the image computer 17 in order to produce a combined MR/PET image.

Corresponding control programs for generating the MR images, PET images and combined MR/PET image, which control programs are stored e.g. on a DVD 21, are selected and the generated images displayed by way of a terminal 13 which comprises a keyboard 15, a mouse 16 and a monitor 14.

Figure 2:
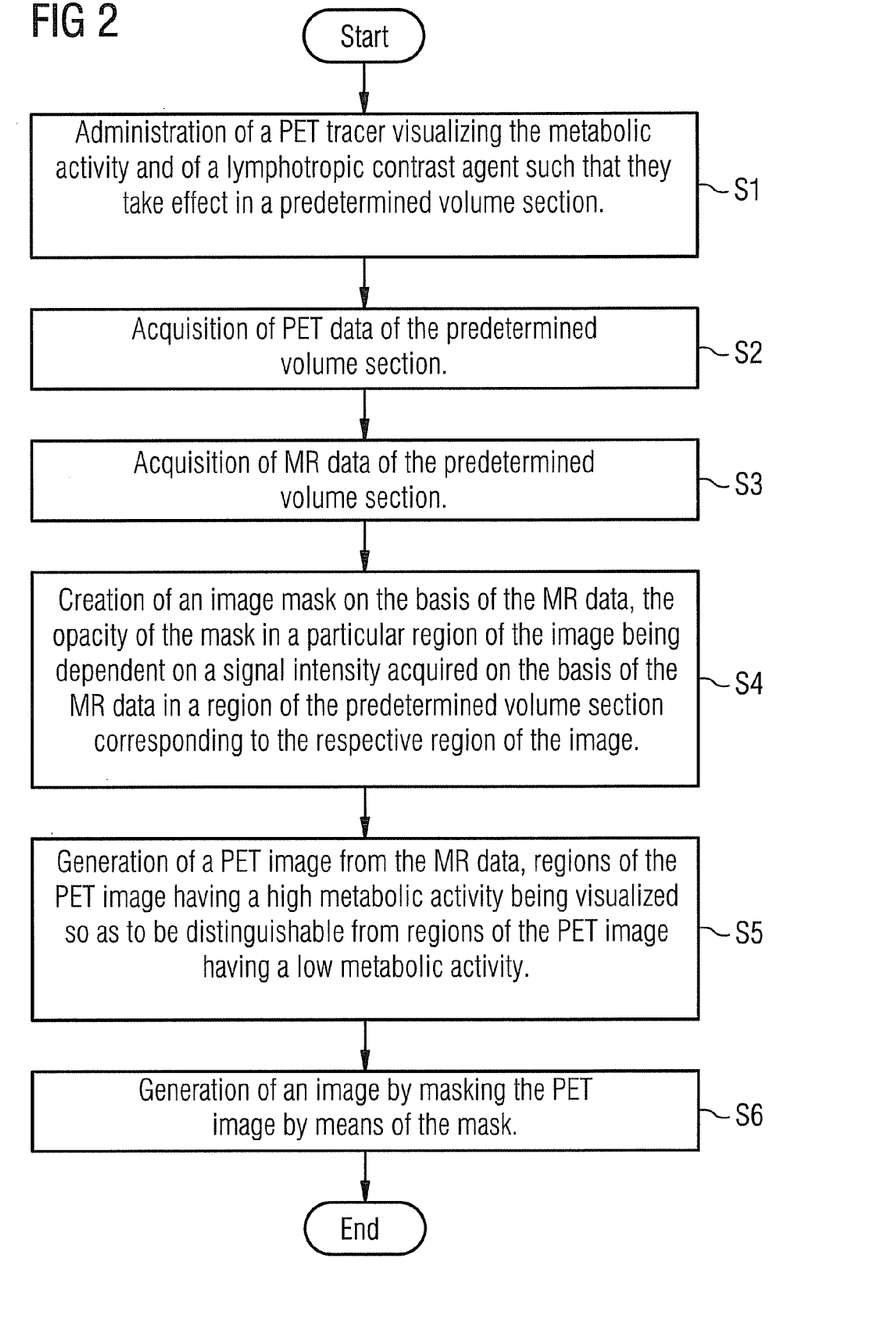
FIG. 2 shows a flowchart of a method according to an embodiment of the invention for generating a combined MR/PET image.

FIG. 2 shows a flowchart of a method according to an embodiment of the invention.

In a first step S1, a PET tracer visualizing the metabolic activity and a lymphotropic contrast agent are administered to a patient O in such a way that the PET tracer and the lymphotropic contrast agent take effect in a predetermined volume section of the patient O.

Next, in a second step S2, the PET data of the predetermined volume section is acquired by way of the positron emission detector 30, and in a third step S3 the MR data of the predetermined volume section is acquired by way of the magnetic resonance system 24.

In this case the two steps S2 and S3 can be performed in any order or also simultaneously.

In the following step S4, an image mask is created on the basis of the MR data. The opacity of the mask in a particular region of the image or mask is dependent in this case on a signal intensity of the corresponding region of the MR image recorded on the basis of the MR data. In other words, starting from the MR data, an MR image is generated from which the mask is then created. The opacity of a specific region of the mask is dependent in this case on the signal intensity of the corresponding region of the MR image. The opacity of a specific region of the mask can in this case be proportional to the signal intensity or inversely proportional to the signal intensity of the corresponding region of the MR image.

In the following step S5, the PET image is generated from the PET data. In this case regions of the PET image which correspond to regions of the predetermined volume section characterized by a high metabolic activity generally have a high signal intensity, while regions of the PET image corresponding to regions of the predetermined volume section characterized by a low metabolic activity usually have a low signal intensity.

In the final step S6, the PET image is masked by way of the mask created in step S4, as a result of which the combined MR/PET image is generated.

An embodiment of the present invention is directed to visualizing lymph nodes in such a way that an abnormal lymph node (in particular a lymph node harboring a malignant disease) can be identified from the visualization (from the image).

An embodiment of the invention is directed to a method for visualizing a lymph node, a combined MR/PET apparatus, a computer program product, and/or by an electronically readable data medium. The dependent claims define preferred and advantageous embodiment variants of the present invention.

Within the scope of an embodiment of the present invention, a method is provided for visualizing a lymph node in a predetermined volume section of an examination subject, i.e. a patient, by way of a combined MR/PET apparatus. An embodiment of the inventive method includes the following:

In a first step, PET data of the predetermined volume section is acquired by way of a positron emission detector, a metabolic activity (e.g. an activity of the glucose metabolism) per PET voxel within the predetermined volume being recorded with the aid of the PET data. In order to record the metabolic activity, in particular a tracer (e.g. fluorodeoxyglucose) is administered prior to the acquisition of the PET data.

In a second step, MR data of the predetermined volume section is acquired by way of a magnetic resonance system, a contrast specific to lymph nodes (i.e. the lymph nodes differ in terms of contrast from the remainder of the predetermined volume section) per region of the predetermined volume being recorded with the aid of the MR data. The lymph-node-specific contrast is achieved in particular through the administration of a lymphotropic contrast agent (iron oxide or perfluorocarbon for example) prior to the acquisition of the MR data.

According to an embodiment of the invention, the first step can be performed before the second step, the second step before the first step or the first step simultaneously with the second step.

In a third step, an image is generated as a function of the metabolic activity recorded per PET voxel and as a function of the lymph-node-specific contrast recorded per region. In the process abnormal lymph nodes are visualized in said image so as to be distinguishable from normal lymph nodes.

An abnormal lymph node is present in particular when the lymph node has at least one of the following features:
an inflammatory change,
a benign tumor,
a fibrotic change,
a malignant tumor.

By way of a combination of the metabolic activity recorded per PET voxel and the lymph-node-specific contrast recorded per region, it is advantageously possible to differentiate abnormal lymph nodes from normal lymph nodes, it also being possible to distinguish lymph nodes characterized by an inflammatory change, lymph nodes characterized by a benign (non-acute) pattern, lymph nodes characterized by a fibrotic change and lymph nodes characterized by a malignant pattern from one another.

In order to generate the image, the signal intensities of an MR image determined from the MR data and the signal intensities of a PET image determined from the PET data can be arbitrarily combined so as to produce the combined MR/PET image in which abnormal lymph nodes can be distinguished from normal lymph nodes and in particular malignant lymph nodes can be distinguished from other lymph nodes. For example, the signal intensities of the PET image can also be added to the signal intensities of the MR image or subtracted therefrom.

According to an example inventive embodiment variant, at least one of the following regions of the image generated according to the invention can be visualized as distinguishable from the remainder of the image:

A first region in which the lymph-node-specific contrast lies above a first MR threshold value and in which the metabolic activity lies above a first PET threshold value.

A second region in which the lymph-node-specific contrast lies above the first MR threshold value and in which the metabolic activity lies below a second PET threshold value.

A third region in which the lymph-node-specific contrast lies below a second MR threshold value and in which the metabolic activity lies below the second PET threshold value.

A fourth region in which the lymph-node-specific contrast lies below the second MR threshold value and in which the metabolic activity lies above the first PET threshold value.

According to this embodiment variant, the first MR threshold value is greater than or equal to the second MR threshold value and the first PET threshold value is greater than or equal to the second PET threshold value.

According to this embodiment variant, all four regions (first to fourth region) can also be visualized as distinguishable from one another in the generated image. Equally it is possible according to an embodiment of the invention that for example only one region (i.e. only the first, only the second, only the third or only the fourth region) is visualized as distinguishable from the remainder of the image.

TABLE

Diagnosis dependent on the MR contrast agent content and on the PET (FDG) activity

| MR contrast agent content | PET (FDG) activity | Diagnosis |
|---|---|---|
| high | high | inflammatory change |
| high | low | benign pattern, non-acute |
| low | low | fibrotic change (conversion) |
| low | high | malignant pattern |

The above table shows a diagnosis for the previously defined four regions. If both the MR contrast agent content and the PET metabolic activity are high (first region), an inflammatory change is present in the corresponding lymph nodes. If moreover the MR contrast agent content is high, but the PET metabolic activity is low (second region), a benign pattern which is non-acute is present. If both the MR contrast agent content and the PET metabolic activity are low (third region), a fibrotic change or a conversion of the corresponding lymph nodes is present. Finally, if the MR contrast agent content is low, but the PET metabolic activity is high (fourth region), a malignant pattern is present in the corresponding lymph nodes.

It is therefore possible according to an embodiment of the invention to visualize lymph nodes as distinguishable in the image generated according to the invention in such a way that a distinction can be made between the four diagnoses cited in the above table for the respective lymph nodes in the image.

According to a further inventive embodiment variant, the image is generated in that, starting from the acquired MR data or starting from the MR image, a mask is generated for the PET data or for the PET image (i.e. an image which is generated on the basis of the PET data). In this case the opacity (non-transparency) of the mask in a specific region of the mask is set as a function of a signal intensity recorded with the aid of the MR data or of an MR contrast agent content recorded with the aid of the MR data in a region of the predetermined volume section corresponding to said region. In this case the image according to an embodiment of the invention is generated as a result of the PET image being masked by the mask.

For example, the opacity in a region of the image or mask can be high/low if the signal intensity of the MR data in the corresponding region of the predetermined volume section is low/high. It is, however, also possible according to an embodiment of the invention for the opacity in a region of the image or mask to be high/low when the signal intensity of the MR data in the corresponding region of the predetermined volume section is high/low.

When iron oxide is used as a lymphotropic contrast agent, a negative contrast is produced. According to the further embodiment variant, a mask is therefore generated in this case from the MR image acquired following the administration of iron oxide, the opacity of the mask resulting from the reciprocal value of the signal intensity of the MR image (i.e. a high signal intensity yields a low opacity). When the mask is placed over a PET image, those lymph nodes in which the MR signal intensity is low are masked because they have a high contrast agent content. Accordingly, lymph nodes characterized by an inflammatory change or a benign pattern are not visible in the image of the further inventive embodiment variant because they are masked by the mask.

Since the signal intensity in the PET image is low due to the low PET metabolic activity in lymph nodes characterized by a fibrotic change and high in lymph nodes characterized by a malignant pattern due to the high PET metabolic activity, the lymph nodes characterized by a malignant pattern have the highest signal intensity overall in the image of the further embodiment variant. In other words, in the image of the further embodiment variant the lymph nodes characterized by malignant patterns stand out distinctly and can clearly be distinguished from the other lymph nodes (including those characterized by a fibrotic change).

The effect of the further embodiment variant can be reinforced further if an MR contrast agent (e.g. gadolinium chelate) is administered which produces an amplification of the signal in the lymph nodes.

When lymphotropic MR contrast agents are used which lead to an increase in signal intensity in the corresponding lymph nodes, the mask according to an embodiment of the invention is constructed in such a way that a high signal intensity in the MR image corresponds to a high opacity in the corresponding region of the mask.

Furthermore it is possible for the lymph nodes in the predetermined volume section to be segmented on the basis of the MR data or on the basis of the MR image (which is generated with the aid of the MR data). Those regions of the mask which do not correspond to any of the segmented lymph nodes can then be generated as opaque, while those regions of the mask which correspond to a segmented lymph node are generated as transparent.

Moreover it is possible according to an embodiment of the invention to identify or segment those lymph nodes which are embedded in fat (e.g. in mesorectal adipose tissue) on the basis of the MR data or by way of the MR image. Since fat tissue exhibits no PET metabolic activity, the PET metabolic activity occurring in a PET voxel can be attributed in full to that lymph node which is located in the corresponding PET voxel. Accordingly, the PET image and therefore also the combined MR/PET image are corrected in such a way that in the case of lymph nodes whose size is less than the size of a PET voxel, the entire activity (more accurately, metabolic activity) in the PET voxel is nonetheless assigned to the corresponding lymph node.

Also provided within the scope of an embodiment of the present invention is a combined MR/PET apparatus for generating an image of a lymph node in a predetermined volume section in an examination subject. In this case the MR/PET apparatus comprises a control unit for controlling a positron emission detector and for controlling a magnetic resonance system and an image computing unit for receiving PET data of the predetermined volume section acquired by the positron emission detector, for receiving MR data of the predetermined volume section recorded by the magnetic resonance system and for generating the image from the PET data and the MR data.

On the basis of the PET data the MR/PET apparatus records a metabolic activity per PET voxel of the predetermined volume section and on the basis of the MR data records a lymph-node-specific contrast per region or section of the predetermined volume section. As a function of the metabolic activity recorded per PET voxel and as a function of the lymph-node-specific contrast recorded per region, the MR/PET apparatus generates an image in which abnormal lymph nodes are visualized as distinguishable from normal lymph nodes.

The advantages of the combined MR/PET apparatus according to an embodiment of the invention in this case substantially correspond to the advantages of the method according to an embodiment of the invention which have been expounded in detail in the foregoing, so a repetition thereof is unnecessary at this juncture.

An embodiment of the present invention also describes a computer program product, in particular a computer program or a piece of software which can be loaded into a memory of a programmable controller or of a computing unit of a combined MR/PET apparatus. All or different above-described embodiments variants of the method according to the invention can be performed by way of the computer program product when the computer program product runs in the controller or control device of the combined MR/PET apparatus. In this case the computer program product possibly requires program segments, e.g. libraries and help functions, in order to implement the corresponding embodiment variants of the methods. In other words, it is intended by way of the claim directed to the computer program product to place under protection in particular a computer program or a piece of software by which one of the above-described embodiment variants of the method according to the invention can be performed or, as the case may be, which implements said embodiment variant. The software in this case can be a source code (e.g. C++) which still has to be compiled (translated) and link-edited or which only needs to be interpreted, or it can be an executable software code which for execution purposes simply needs to be loaded into the corresponding computing unit.

Finally, at least one embodiment of the present invention discloses an electronically readable data medium, e.g. a DVD, a magnetic tape or a USB stick on which electronically readable control information, in particular software (cf. above), is stored. When the control information (software) is read from the data medium and stored in a controller or computing unit of a combined MR/PET apparatus, all the inventive embodiment variants of the above-described method can be performed.

An embodiment of the present invention is suitable in particular for the acquisition and generation of images on which lymph nodes characterized by a malignant pattern are visualized as distinguishable from other lymph nodes or from the remainder of the image. It goes without saying that the present invention is not limited to this preferred field of application, since it is also possible according to an embodiment of the invention for example to generate images on which fibrotically changed lymph nodes or lymph nodes exhibiting an inflammatory change can be visualized as distinguishable. Furthermore the principle according to an embodiment of the invention can also be used in the diagnosis of other organs (not lymph nodes).

LIST OF REFERENCE SIGNS

1 Basic field magnet
2 Shim coil
3 Gradient field system
4 RF antenna
5 Combined MR/PET apparatus
6 Duplexer
7 Amplifier
8, 8 Receive channel
9 Transmit channel
10 Control device
11 Output
12 Input
13 Terminal
14 Monitor
15 Keyboard
16 Mouse
17 Image computer
18 Sequence controller
19 Synthesizer
20 System computer
21 DVD
22 Table
23 Patient support
24 Magnetic resonance system
30 Positron emission detector
O Examination subject or patient
S1-S6 Method step

What is claimed is:

1. A method for visualizing lymph nodes in a volume section of an examination subject by way of a combined MR/PET apparatus, the method comprising:
    acquiring PET data of the volume section, by way of a positron emission detector, to record, on the basis of the acquired PET data, a metabolic activity per PET voxel within the volume section;
    acquiring MR data of the volume section, by way of a magnetic resonance system, to record, on the basis of the acquired MR data, a lymph-node-specific contrast per region of the volume section; and
    generating an image as a function of metabolic activity recorded per PET voxel and as a function of the lymph-node-specific contrast recorded per region, abnormal lymph nodes being visualized in the image as being distinguishable from normal lymph nodes, wherein at least one of a plurality of predefined regions, each associated with a respective lymph node diagnosis, is identified in the image, the image generated to present said at least one identified predefined region as being visually distinguishable from a remainder of the image, wherein said plurality of predefined regions comprise of:
    a region in which the lymph-node-specific contrast lies above a first set MR threshold value and in which the metabolic activity lies above a first set PET threshold value,
    a region in which the lymph-node-specific contrast lies above the first set MR threshold value and in which the metabolic activity lies below a second set PET threshold value,
    a region in which the lymph-node-specific contrast lies below a second set MR threshold value and in which the metabolic activity lies above the fn'st set PET threshold value, and
    a region in which the lymph-node-specific contrast lies below the second set MR threshold value and in which the metabolic activity lies below the second set PET threshold value,
    wherein the first set MR threshold value is greater than or equal to the second set MR threshold value,
    the first set PET threshold value is greater than or equal to the second set PET threshold value, and
    the first and second set MR threshold values are set separately from the first and second set PET threshold values; and
    displaying the generated image.

2. The method as claimed in claim 1, wherein the metabolic activity within the volume section is recorded on the basis of the PET data in that a corresponding tracer is administered to the examination subject prior to the acquisition of the PET data.

3. The method as claimed in claim 2, wherein the tracer is fluorodeoxyglucose.

4. The method as claimed in claim 1, wherein the lymph-node-specific contrast is recorded on the basis of the MR data in that a lymphotropic contrast agent is administered to the examination subject prior to the acquisition of the MR data.

5. The method as claimed in claim 4, wherein the lymphotropic contrast agent is iron oxide or perfluorocarbon.

6. A non-transitory electronically readable data medium, on which is stored electronically readable control information which is embodied in such a way that when the data medium is used in a control device of a combined MR/PET apparatus, the control information performs the method as claimed in claim 1.

7. The method as claimed in claim 1, wherein the image is generated in that a mask is created for the PET data on the basis of the acquired MR data, opacity of the mask in a region of the image is set as a function of a signal intensity recorded on the basis of the MR data in a region of the volume section corresponding to said region, a PET image is generated from the PET data, and the image is generated in that the PET image is masked by way of the mask.

8. The method as claimed in claim 7, wherein the opacity in a region of the image is high if the signal intensity of the MR data in a region of the volume section corresponding to said region is high, or the opacity in a region of the image is low if the signal intensity of the MR data in a region of the volume section corresponding to said region is high.

9. The method as claimed in claim 8, wherein lymph nodes in the volume section are segmented on the basis of the MR data, and regions of the mask which correspond to none of the segmented lymph nodes are generated as opaque.

10. A non-transitory computer readable medium including program segments for, when executed on a computer device, causing the computer device to implement the method of claim 1.

11. The method of claim 1, wherein the following regions of the image are distinguishable from a remainder of the image,
the region in which the lymph-node-specific contrast lies above the first set MR threshold value and in which the metabolic activity lies above the first set PET threshold value,
the region in which the lymph-node-specific contrast lies above the first set MR threshold value and in which the metabolic activity lies below the second set PET threshold value,
the region in which the lymph-node-specific contrast lies below the second set MR threshold value and in which the metabolic activity lies above the first set PET threshold value, and
the region in which the lymph-node-specific contrast lies below the second set MR threshold value and in which the metabolic activity lies below the second set PET threshold value.

12. The method of claim 1, wherein each of the plurality of predefined regions are visually distinguishable from each other and the remainder of the image.

13. A method as for visualizing lymph nodes in a volume section of an examination subject by way of a combined MR/PET apparatus, the method comprising:
acquiring PET data of the volume section, by way of a positron emission detector, to record, on the basis of the acquired PET data, a metabolic activity per PET voxel within the volume section;
acquiring MR data of the volume section, by way of a magnetic resonance system, to record, on the basis of the acquired MR data, a lymph-node-specific contrast per region of the volume section; and
generating an image as a function of metabolic activity recorded per PET voxel and as a function of the lymph-node-specific contrast recorded per region, abnormal lymph nodes being visualized in the image as being distinguishable from normal lymph nodes, wherein lymph nodes which are embedded in fat are segmented on the basis of the acquired MR data, a size of the segmented lymph nodes is determined, and an activity within a PET voxel recorded on the basis of the acquired PET data is assigned in full to a volume of a segmented lymph node recorded within the PET voxel if the size of the segmented lymph node is less than a size of the PET voxel, and the image generated to present at least one of the following regions of the image as being visually distinguishable from a remainder of the image:
a region in which the lymph-node-specific contrast lies above a first MR threshold value and in which the metabolic activity lies above a first PET threshold value,
a region in which the lymph-node-specific contrast lies above the first MR threshold value and in which the metabolic activity lies below a second PET threshold value,
a region in which the lymph-node-specific contrast lies below a second MR threshold value and in which the metabolic activity lies above the first PET threshold value, and
a region in which the lymph-node-specific contrast lies below the second MR threshold value and in which the metabolic activity lies below the second PET threshold value,
wherein the first MR threshold value is greater than or equal to the second MR threshold value, and
the first PET threshold value is greater than or equal to the second PET threshold value; and
displaying the generated image.

14. A combined MR/PET apparatus for generating an image of a lymph node in a volume section of an examination subject, the MR/PET apparatus comprising:
a controller configured to control a positron emission detector of the MR/PET apparatus to record a metabolic activity per PET voxel of the volume section on the basis of PET data and to control a magnetic resonance system of the MR/PET apparatus to record a lymph-node-specific contrast per region of the volume section on the basis of MR data; and
an image computer configured to receive the PET data of the volume section acquired by the positron emission detector, to receive the MR data of the volume section recorded by the magnetic resonance system and to generate the image from the PET data and the MR data, wherein the image is generated as a function of the metabolic activity recorded per PET voxel and as a function of the lymph-node-specific contrast recorded per region, abnormal lymph nodes being visualized as distinguishable in the image from normal lymph nodes, wherein at least one of a plurality of predefined regions, each associated with a respective lymph node diagnosis, is identified in the image, the image generated to present said at least one identified predefined region as being visually distinguishable from a remainder of the image, wherein said plurality of predefined regions comprise of:
a region in which the lymph-node-specific contrast lies above a first set MR threshold value and in which the metabolic activity lies above a first set PET threshold value, a region in which the lymph-node-specific contrast lies above the first set MR threshold value and in which the metabolic activity lies below a second set PET threshold value, a region in which the lymph-node-specific contrast lies below a second set MR threshold value and in which the metabolic activity lies above the first set PET threshold value, and a region in which the lymph-node-specific contrast lies below the second set MR threshold value and in which the metabolic activity lies below the second set PET threshold value, wherein the first set MR threshold value is greater than or equal to the second set MR threshold value, the first set PET threshold value is greater than or equal to the second set PET threshold value, and the first and second set MR threshold values are set separately from the first and second set PET threshold values.

15. The combined MR/PET apparatus of claim 14, wherein the following regions of the image are distinguishable from a remainder of the image, the region in which the lymph-node-specific contrast lies above the first set MR threshold value and in which the metabolic activity lies above the first set PET threshold value, the region in which the lymph-node-specific contrast lies above the first set MR threshold value and in which the metabolic activity lies below the second set PET threshold value, the region in which the lymph-node-specific contrast lies below the second set MR threshold value and in which the metabolic activity lies above the first set PET threshold value, and the region in which the lymph-node-specific contrast lies below the second set MR threshold value and in which the metabolic activity lies below the second set PET threshold value.

16. A non-transitory computer program product including a program, directly loadable into a memory of a programmable controller device of a combined MR/PET apparatus, the computer program product comprising program segments for performing the method as claimed in claim 1 when the program is executed in the programmable controller device of the combined MR/PET apparatus.

* * * * *